US00PP08047P

United States Patent [19]

van der Knaap

[11] Patent Number: Plant 8,047

[45] Date of Patent: Nov. 24, 1992

[54] CHRYSANTHEMUM PLANT — MAJOOR BOSSHARDT CULTIVAR

[75] Inventor: Jacques C. M. van der Knaap, De Lier, Netherlands

[73] Assignee: Fides Beheer B.V., De Lier, Netherlands

[21] Appl. No.: 680,136

[22] Filed: Apr. 3, 1991

[51] Int. Cl.[5] ..... A01H 5/00

[52] U.S. Cl. ..... Plt./77

[58] Field of Search ..... Plt./74, 74.1, 82.1, Plt./77

[56] References Cited

U.S. PATENT DOCUMENTS

P.P. 6,103 2/1988 van der Knaap ..... Plt. 74

P.P. 6,240 8/1988 van der Knaap ..... Plt. 74

*Primary Examiner*—Howard J. Locker

*Attorney, Agent, or Firm*—Burns, Doane, Swecker & Mathis

[57] ABSTRACT

A new and distinct cultivar of Chrysanthemum plant named Majoor Bosshardt is provided. The new cultivar was the result of a controlled breeding program wherein an unnamed plant designated 83.660 was pollinated by the Daymark cultivar (U.S. Plant Pat. No. 6,240). More specifically, the new cultivar forms attractive large white anemone-centered flowers having white ray florets and a green center when immature. The inflorescence tends to be pyramidal in configuration. The response period of the flowers is approximately eight weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium,* Ramat., and hereinafter is referred to by the cultivar name Majoor Bosshardt.

The new cultivar is the product of a planned breeding program which had as its objective the creation of a new Chrysanthemum cultivar which exhibits attractive relatively large white flowers having a green center when immature, exhibits a flower response period of approximately eight weeks, and possesses the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1986 at De Lier, The Netherlands. The female parent (i.e., the seed parent) was an unnamed plant designated 83.660 and the male parent (i.e., the pollen parent) was the Daymark cultivar (U.S. Plant Pat. No. 6,240). The parentage of the new cultivar can be summarized as follows:

83.660×Daymark.

The seeds resulting from the above pollination were sown and plantlets were obtained which were physically and biologically different from each other. Selective study resulted in the identification of a single plant of the new variety.

It was found that the new cultivar of the present invention:

(a) exhibits attractive relatively large anemone-centered flowers having an overall diameter of approximately 60 to 65 mm. wherein the ray florets are white and the flower center comprising the disc florets is green in coloration when immature, (b) bears flowers in a somewhat pyramidal configuration, (c) exhibits a flower response period of approximately eight weeks, (d) forms dark green foliage, and (e) has the ability to produce flowers of commercially acceptable quality throughout the year in a cut mum production program.

The keeping quality of the flowers is good, and partial resistance to leafminer is exhibited by the new cultivar.

Asexual reproduction of the new cultivar by cuttings initially taken during June, 1986, as performed at De Lier, The Netherlands, in a controlled environment has demonstrated that the characteristics of the new cultivar as herein disclosed are firmly fixed and are retained through successive generations of asexual propagation.

Majoor Bosshardt has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Daymark parent (U.S. Plant Pat. No. 6,240) and the Puma cultivar (U.S. Plant patent application Ser. No. 07/680,137, filed concurrently herewith), the following characteristics are observed:

| | MAJOOR BOSSHARDT | DAYMARK | PUMA |
|---|---|---|---|
| Diameter of Flower: | Approximately 60 to 65 mm. | Approximately 70 to 75 mm. | Approxiamately 40 to 45 mm. |
| Diameter of Disc: | Approximately 17 mm. | Approximately 22 mm. | Approximately 22 mm. |
| Length of Petals: | Approximately 30 to 35 mm. | Approximately 40 to 45 mm. | Approximately 20 to 22 mm. |

-continued

| | MAJOOR BOSSHARDT | DAYMARK | PUMA |
|---|---|---|---|
| Foliage Color: | Darkest Green | Medium/Dark Green | Paler Green |
| Foliage Size: | Approximately 80 × 70 mm. | Approximately 100 × 70 mm. | Approximately 80 × 60 mm. |
| Response: | Slightly Slower | Quicker | Quicker |

Also, at the harvest stage one can observe a disparity in the development of the petaloids at the flower center. More specifically, such petaloid development ranges from the most to the fewest in the following order: (1) Puma, (2) Daymark, and (3) Majoor Bosshardt.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during October, 1989. The plants described were grown under standard greenhouse conditions which approximate those commonly utilized for the production of cut mums.

Classification:

*Botanical.*—*Dendranthema morifolium* Ramat., cv. Majoor Bosshardt.

*Commercial.*—Cut anemone spray.

Inflorescence

A. Capitulum:

*Form.*—Pyramidal.

*Type.*—Anemone.

*Diameter across face.*—Approximately 60 to 65 mm. on average.

*Diameter of disc.*—Approximately 17 mm. on average.

*Length of petals.*—Approximately 30 to 35 mm. on average.

B. Corolla of ray and disc florets:

*Color (General tonality from a distance of three meters).*—White.

*Color ray florets.*—(Top surface). — White Group 155D.

*Color disc florets.*—Yellow-Green Group 150A when immature changing to yellow when mature.

C. Reproductive organs:

*Androecium.*—Present in disc florets.

*Gynoecium.*—Present in both disc florets and ray florets.

Plant

A. General appearance:

*Height.*—Approximately 100 cm. on average.

B. Foliage:

*Color (upper surface).*—Yellow-Green Group 147A.

*Color (under surface).*—Yellow-Green Group 147B.

*Size.*—Approximately 80×70 mm.

I claim:

1. A new and distinct cultivar of Chrysanthemum plant named Majoor Bosshardt, substantially as herein shown and described, which:

(a) exhibits attractive relatively large anemone-centered flowers having an overall diameter of approximately 60 to 65 mm. wherein the ray florets are white and the flower center comprising the disc florets is green in coloration when immature, (b) bears flowers in a somewhat pyramidal configuration, (c) exhibits a flower response period of approximately eight weeks, (d) forms dark green foliage, and (e) has the ability to produce flowers of commercially acceptable quality throughout the year in a cut mum production program.

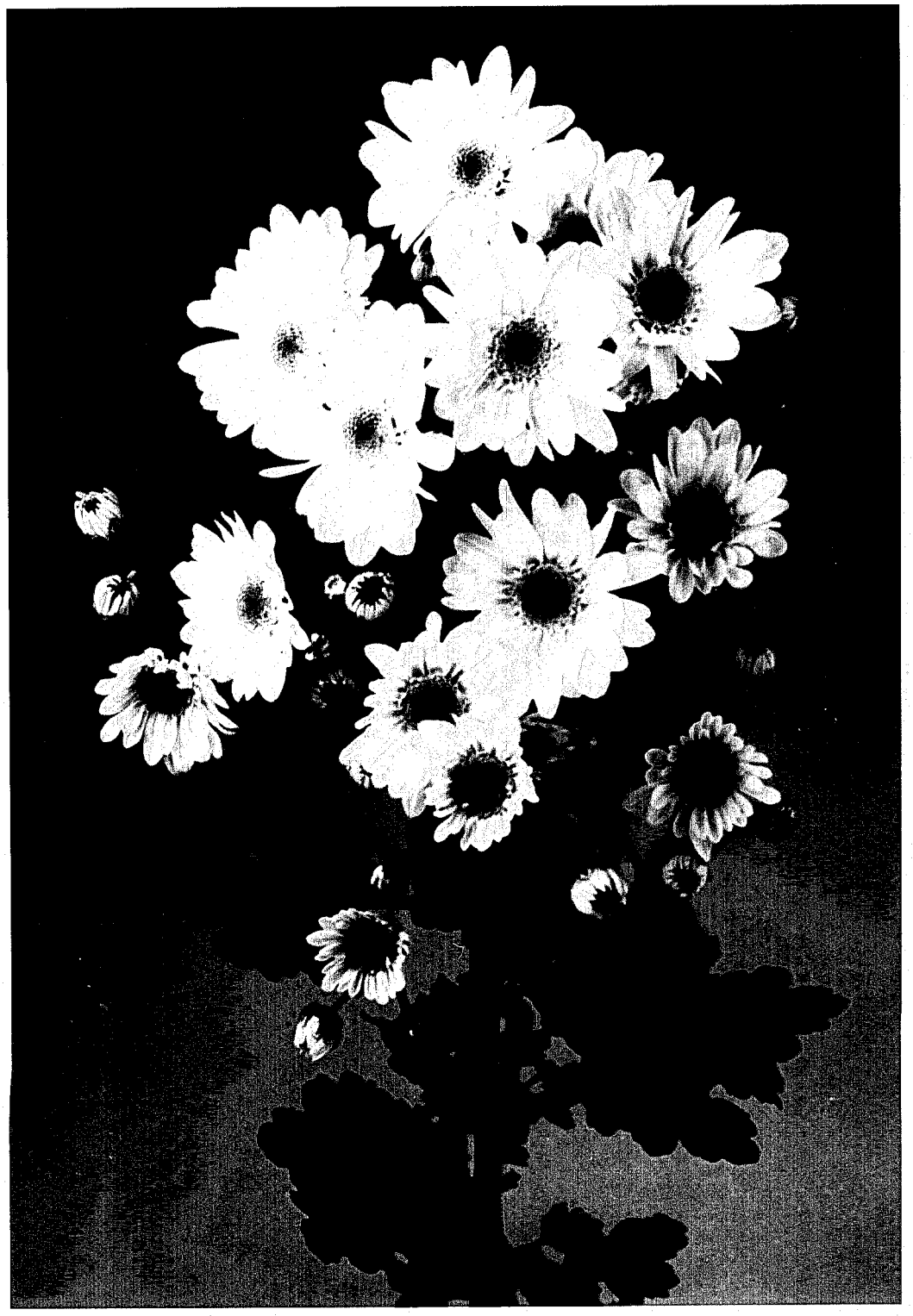

* * * * *